(12) United States Patent
Kadir et al.

(10) Patent No.: US 8,396,266 B2
(45) Date of Patent: Mar. 12, 2013

(54) CHARACTERISATION OF FUNCTIONAL MEDICAL IMAGE SCANS

(75) Inventors: Timor Kadir, Oxford (GB); Veit Ulrich Schenk, Oxford (GB)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1156 days.

(21) Appl. No.: 11/785,921

(22) Filed: Apr. 20, 2007

(65) Prior Publication Data

US 2007/0287906 A1 Dec. 13, 2007

(30) Foreign Application Priority Data

Apr. 21, 2006 (GB) .................................. 0607910.7

(51) Int. Cl.
*G06K 9/00* (2006.01)
(52) U.S. Cl. ......... 382/128; 382/100; 382/131; 382/132
(58) Field of Classification Search .................. 382/100, 382/128–132
See application file for complete search history.

(56) References Cited

U.S. PATENT DOCUMENTS 6,740,883 B1 * 5/2004 Stodilka et al. .......... 250/363.04
2004/0236216 A1 * 11/2004 Manjeshwar et al. ........ 600/436

OTHER PUBLICATIONS

J. A.D. Aston, R.N. Gunn, K.J. Worsley, Y. Ma, A.C. Evans, and A. Dagher, "A Statistical Method for the Analysis of Positron Emission Tomography Neuroreceptor Ligand Data," Neuroimage, vol. 12, Issue 3, Sep. 2000, pp. 245-256.*
I. Buvat, I. Castiglioni, "Monte Carlo simulations in SPET and PET," The Quarterly Journal of Nuclear Medicine; vol. 46 No. 1, Mar. 2002, pp. 48-61.*
Ma, Y., and Evans, A.C. "Analytical modeling of PET imaging with correlated functional and structural images," IEEE Transactions on Nuclear Science, vol. 44, No. 6, Dec. 1997, pp. 2439-2444.*
Andreas Markus Loening, Sanjiv Sam Gambhir, "AMIDE: A Free Software Tool for Multimodality Medical Image Analysis," Molecular Imaging. vol. 2, No. 3, Jul. 2003, pp. 131-137.*
Irene Buvat, Isabella Castiglioni, Juliette Feuardent, and Maria-Carla Gilardi, "Unified description and validation of Monte Carlo," Physics in Medicine and Biology, vol. 50, 2005, pp. 329-346.*
S Jan, G Santin, D Strul, S Staelens, K Assi'e et al. "GATE: a simulation toolkit for PET and SPECT," Physics in Medicine and Biology, vol. 49, 2004, pp. 4543-4561.*
Anthonin Reilhac, Gaël Batan, Christian Michel, Christophe Grova, Jussi Tohka, D. Louis Collins, Nicolas Costes, and Alan C. Evans, "PET-SORTEO: Validation and Development of Database of Simulated PET Volumes," IEEE Transactions on Nuclear Science, vol. 52, No. 5, Oct. 2005.*
Jesper L.R. Andersson, Anders Sundin and Sven Valind, "A Method for Coregistration of PET and MR Brain Images" The Journal of Nuclear Medicine, vol. 36, No. 7, 1995, pp. 1307-1315.*

(Continued)

*Primary Examiner* — Eric Rush
(74) *Attorney, Agent, or Firm* — Crowell & Moring LLP

(57) ABSTRACT

In a method for assessing an acquired functional medical scan, a virtual functional medical scan is generated from a structural medical scan (e.g., MRI) using known techniques. The acquired functional medical image scan is then assessed by comparing it with the virtual functional medical scan. Since both scans are derived from the same source, there is no need for e.g., registration of the patient anatomy and the reference data.

17 Claims, 4 Drawing Sheets

OTHER PUBLICATIONS

C. Grove, P. Jannin, A. Biraben, I. Buvat, H. Benali, A. M. Bernard, J. M. Scarabin and B. Gibaud, "A methodology for generating normal and pathological brain perfusion SPECT images for evaluation of MRI/SPECT fusion methods: application in epilepsy", Physics in Medicine and Biology, vol. 48 No. 24, Dec. 2003, pp. 4023-4043.*

Reilhac, A. et al., "PET-SORTEO: A Monte Carlo-Based Simulator With High Count Rate Capabilities", IEEE Transactions on Nuclear Science, Feb. 2004, vol. 51, No. 1, pp. 46-52.

Pajevic, S. et al., "Noise Characteristics of 3-D and 2-D PET Images", IEEE Transactions on Medical Imaging, Feb. 1998, vol. 17, No. 1, pp. 9-23.

Fessler, J. A., "Mean and Variance of Implicitly Defined Biased Estimators (Such as Penalized Maximum Likelihood): Applications to Tomography", IEEE Transactions on Image Processing, Mar. 1996, vol. 5, No. 3, pp. 493-506.

Dahlbom, M., "Estimation of Image Noise in PET Using the Bootstrap Method", IEEE Transactions on Nuclear Science, Oct. 2002, vol. 49, No. 5, pp. 2062-2066.

Dahlbom, M. et al., "Comparison of Noise Equivalent Count Rates and Image Noise", IEEE Transactions on Nuclear Science, Oct. 2005, vol. 52, No. 5, pp. 1386-1390.

Carson, R. E. et al., "An Approximation Formula for the Variance of PET Region-of-Interest Values", IEEE Transactions on Medical Imaging, Jun. 1993, vol. 12, No. 2, pp. 240-250.

Hertzmann, A. et al., "Image Analogies", International Conference on Computer Graphics and Interactive Techniques, 2001.

* cited by examiner

CHARACTERISATION OF FUNCTIONAL MEDICAL IMAGE SCANS

FIELD OF THE INVENTION

The invention is concerned with the assessment of functional medical scans such as Positron Emission Tomography scans, typically for the purpose of assessing disease state or characterizing abnormal drug or tracer uptake.

BACKGROUND OF THE INVENTION

Medical imaging techniques may be characterized as structural or functional. Structural scanning methods such as X-ray based procedures (including Computerized Tomography (CT) scanning) and Magnetic Resonance Imaging (MRI) provide anatomical information about a subject but yield little information concerning biochemical processes or metabolism. Functional techniques such as Positron Emission Tomography (PET) or Single Photon Emission Computed Tomography (SPECT) provide such information by indicating the uptake of a suitably radiolabelled tracer throughout the body of a patient.

To assess a nuclear medicine (NM) scan (PET or SPECT), the clinician needs to have a good understanding of the normal distribution of the radio labelled tracer and the characteristic patterns of uptake from various pathological conditions. The fact that NM images describe function, and not anatomy, adds further difficulty in the assessment as abnormal functional pattern needs to be correlated to any existing abnormal anatomy.

The assessment process involves comparison of the functional scan with the underlying anatomy, which can be obtained from an MRI or CT scan. Software fusion tools or hardware devices can assist in bringing the two images in geometric alignment, but the assessment of the two scans in combination remains the task of the clinician: the exact impact of abnormal anatomy on function is difficult to estimate mentally and the mapping between anatomical information and functional information remains essentially subjective.

The functional scan must also be compared with normal patterns of uptake and known pathological conditions. Other software tools to assist in this step, which have started to appear on the clinical market, compare the patient scan with a database of normal patient scans in order to detect statistically significant abnormalities. This type of comparison has limitations as many individual variations are diluted when comparing with the average of multiple patients. Techniques to try and overcome this problem with methods like partial volume correction alleviate the problem to some extent by trying to model and correct the influence of anatomical variations on the functional uptake. However, they are difficult to interpret as their result depends highly on the quality of the registration between the anatomical scan and the functional scan.

Techniques are known for the simulation of functional scans using data acquired during a structural scan. One such algorithm for PET functional images is PET-SORTEO (A. Reilhac, C Lartizien, N. Costes, S. Sans, C. Comtat, R. N. Gunn and A. C. Evans, "PET-SORTEO: A Monte Carlo-based simulator with high count rate capabilities", IEEE Trans. Nucl. Sci., vol. 51 no. 1, pp 46-52, February 2004) which is a realistic PET simulator modeling the positron annihilation as they happen in the imaged object, and the detection process by the detectors.

The technique works by:
1) segmenting the structural scan into a number of tissue classes; for example grey-matter, white matter, scalp, cerebro-spinal fluid (CSF) for the brain, or even finer sub-structures of the brain (cortical temporal lobe, parietal lobe, basal ganglia, etc.). (FIG. 2, Step 202)
2) Assigning an individual Time-Activity Curve (TAC), which represents the activity of the tracer uptake as a function of time, to each tissue class. This TAC is modeled from such factors as the tracer itself and tissue type. This is supplied by the user, but a range of normal values could be obtained from experimental protocols. (Step 204)
3) For each class, a series of discrete events is modeled and tracked through to detection in a virtual scanner corresponding to a similar protocol to that used in a real acquired scan. The simulation includes factors such as the scanner type, detector geometry, crystal type, electronic circuit performance, injection-volume of the tracer, etc. (Step 206)

The results of functional scans (e.g., functional images), such as those acquired using fluorine-18 2-fluoro-2-deoxy-D-glucose-PET (FDG-PET), can be used to determine the drug-uptake in certain regions or the disease state of a certain anatomical region. Often these images cannot be used directly in a quantitative fashion since the tracer uptake depends on a number of factors, such as patient physiology, the equipment used for scanning and amount of biomarker injected. One solution to this problem is first to normalize the scans prior to comparison with a reference of normal uptake.

Normalization typically consists of two steps: the first seeks to adjust the intensity values of the scan to compensate for patient perfusion, metabolism, imaging protocol and scanner variability; the second, registration step, transforms the scan spatially into a common reference coordinate system to compensate for differences between the patient anatomy and that of the average or reference normal.

The reference of normal uptake can be typically generated by applying the steps of normalization to a corpus of normal scans and combining these to generate some kind of average scan.

For example, in the case of assessing FDG-PET scans for assessing Alzheimer's disease, a typical approach is to build a reference average which consists of the mean and standard deviation of a number of Asymptomatic Control (AC) scans which are "normalized" as described above. A patient case scan can then be compared with the reference average for example by computing a score of normality (for instance, a Z-score, or a number of standard deviations) for each voxel, thereby assessing the likelihood of a particular voxel being normal or arising as a result of a disease state.

There are a number of problems associated with this approach:
1) It is often difficult to obtain enough representative AC data from clinical sites (because PET scans are not normally taken from normal, healthy individuals); to build the statistical model, many reference subjects would be needed (more than 30 subjects per class of population (male, female, various age groups)). Even the choice of what is 'normal' presents difficulties as this is subjective;
2) A deformable registration step is necessary which maps the novel patient scan to the reference normal space. This never perfectly compensates for individual variations as the images have a limited resolution and deformable registration is a very difficult problem to solve. Errors in the registration may result in different anatomical regions being compared which can lead to significant errors in estimation of the score of normality.

3) The reference average model often does not capture all of the anatomic and functional variation of the AC data, leading to false positives. This is due to the use of over simplistic models used to represent the reference average. For example, some patients may have a bigger cerebellum than the population average; some may have wider Sylvian fissures, etc.

4) Data must be acquired from several sites using different scanners and, or acquisition protocols to avoid the reference average becoming very specific to a particular equipment setting or hospital practice. However, this may lead to a weakening of the reference average and loss of sensitivity of the comparison since these factors are not due to patient variations.

SUMMARY OF THE INVENTION

The present invention provides a method of generating a data set representative of a disease state or drug or tracer uptake of a subject, from an acquired actual functional medical image scan, by comparing it with a synthesized functional medical image scan generated from a structural medical image scan acquired from the same subject.

Other objects, advantages and novel features of the present invention will become apparent from the following detailed description of the invention when considered in conjunction with the accompanying drawings.

DETAILED DESCRIPTION OF THE INVENTION

Figure 1:
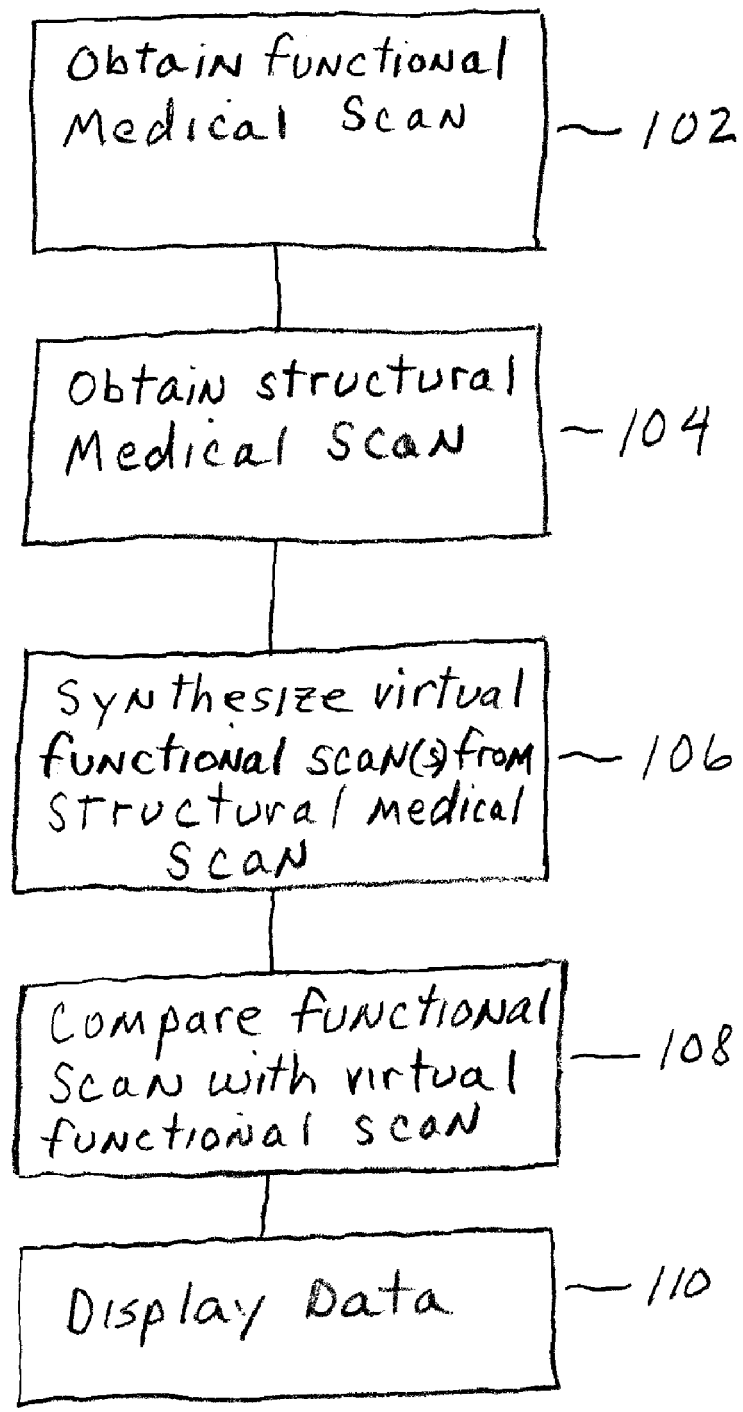
FIG. 1 is a flow chart that illustrates an embodiment of the method according to the invention.
Figure 2:
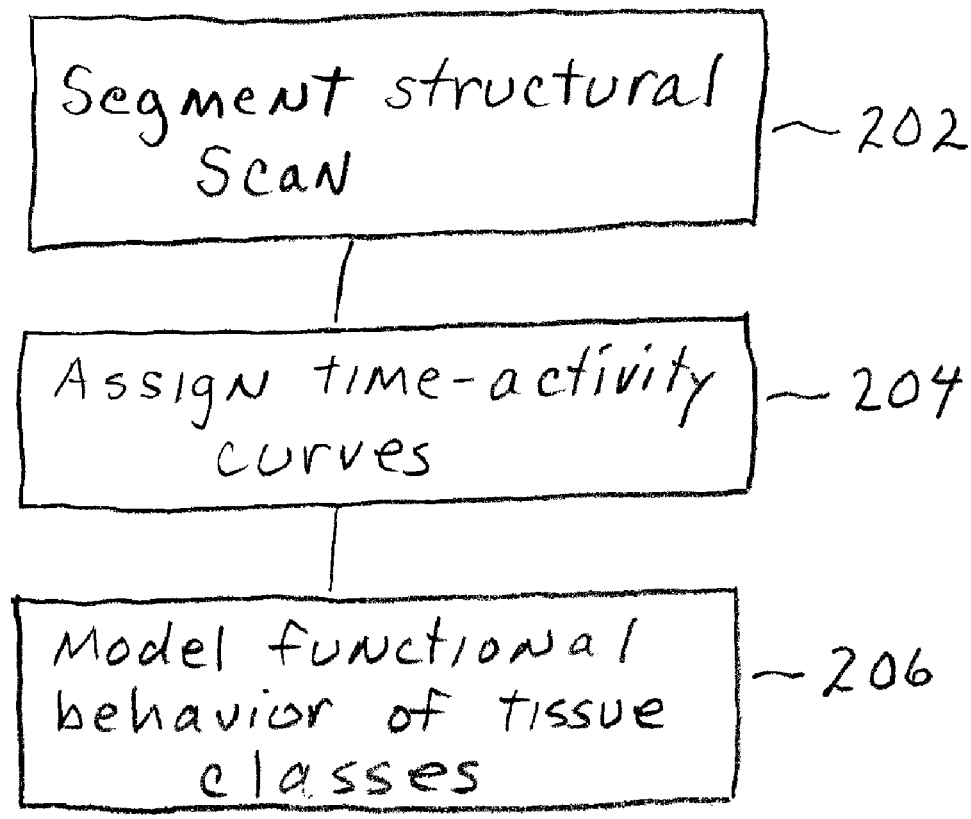
FIG. 2 shows the steps of a process for generating a virtual functional medical scan.

As shown in FIG. 1, the invention overcomes the problems associated with previous attempts to interpret the results of functional scans, by synthesizing a functional scan (Step 106) to produce a virtual functional scan for a particular patient and scanner, using a structural medical scan (Step 104) and a simulation method that can generate a virtual functional scan from the structural information. An actual functional scan (Step 102) and a virtual functional scan are generated from the same source (the same anatomy as imaged in the structural scan) and hence they can be compared directly (Step 108) without encountering the problems outlined previously. The resulting data set can then be displayed as a graphical image (Step 110).

The method of the invention can comprise comparison of the actual functional scan with a virtual functional scan generated for normal states or diseased states. Since the exact parameters used for the acquisition of the actual functional scan (scanner type, acquisition protocol etc.) in Step 102 are used in the simulation, the actual functional scan and the virtual functional scan can be compared directly (Step 108).

In a simple embodiment of the invention, the actual functional medical scan is compared to a virtual functional scan for the purpose of determining whether the two scans differ significantly. In a more sophisticated embodiment, a corpus of virtual functional scans can be generated. The corpus could be used to generate a statistical reference database in the conventional manner and can be obtained either by running the simulation many times with the same parameters or by varying the TACs, scanner or other parameters. A reference average virtual functional scan is then generated which is patient specific.

In another embodiment, some disease specific TACs are utilized to simulate a particular disease state. A number of disease states can be simulated and the patient scan compared to the resultant virtual functional scans: finding the scans which give most correlation may give an indication of the disease type (if a number of diseases is simulated) or the disease progression state (if a number of progression states of the same disease is simulated).

In another embodiment, the method of the invention may be used to compare uptake in different regions of the body and with different structural and functional modalities. This is useful for assessing drug or tracer uptake rather than assessing disease state.

The invention overcomes the problems associated with the prior art because the virtual functional scan is specific for the patient, functional scanning machine and protocol.

The registration problem is easier to solve since there is no longer anatomical variation to deal with when aligning the real functional scans and the virtual functional scan. Spatial registration between the virtual functional scan and the patient scan is rigid as it comes from the same patient, as opposed to deformable as is required with the conventional methods where the patient's scan needs to be aligned to that of another person's (or to an average of a number of scans from different people). Rigid registration is a much easier problem to solve than deformable and there are a number of existing techniques available.

Since the virtual functional scan can be made scanner specific, these variables have also been factored out of the comparison such that scanner type/geometry, reconstruction parameters, injection-dose are those used for the actual functional scan.

Finally, there is no need to obtain a large corpus of AC data nor is there a need to build an accurate model.

It should be noted that in a clinical hospital practice, the structural (MR or CT) scan would be acquired before the functional scan (PET or SPECT): typically a few days would separate the two acquisitions. It could therefore be envisaged that the necessary simulations (which may take some amount of time) be run on a server before the patient is scheduled for the functional scan and are ready for when the real functional scan is acquired and evaluated.

Although the description of the invention thus far refers to an existing PET simulator, there is no limitation to this modality as similar simulators for other modalities such as SPECT, fluorescence imaging etc could be developed. The process would remain the same and the invention equally applicable.

Figure 3:
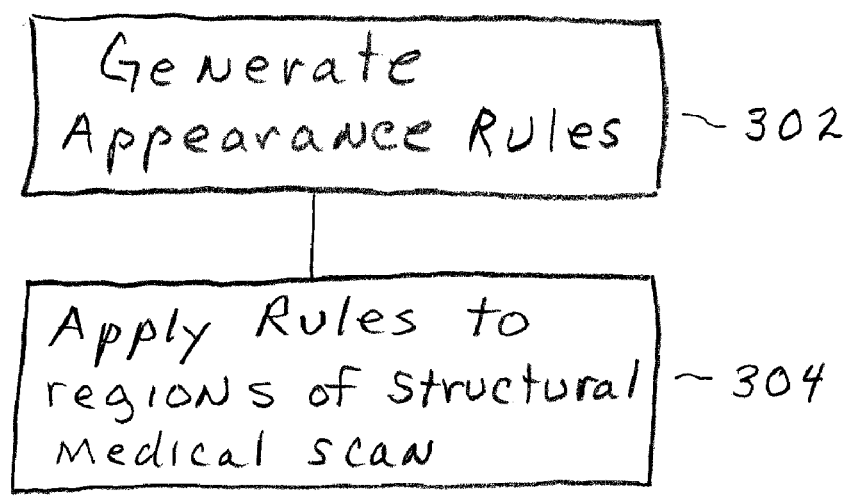
FIG. 3 shows an alternative process for generating a virtual medical scan.
Figure 4:
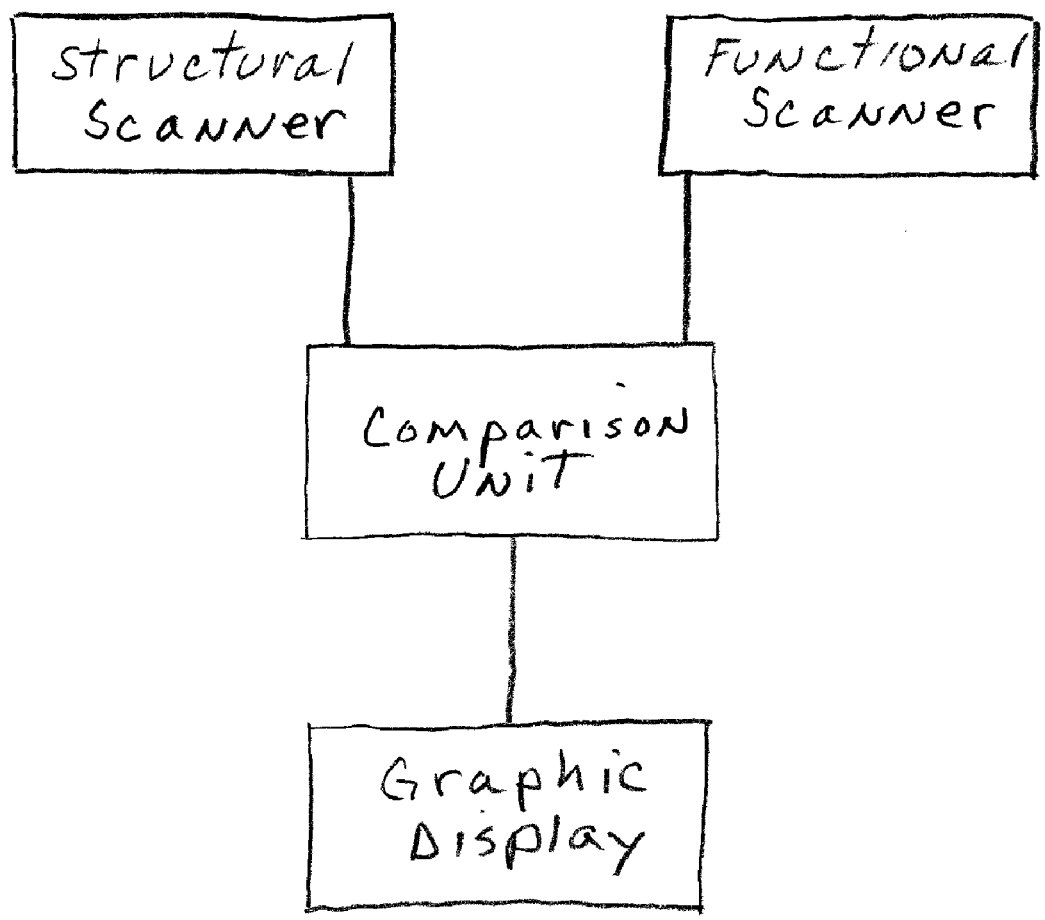
FIG. 4 is a schematic diagram of an embodiment of the apparatus according to the invention.

Moreover, alternative methods of generating the virtual functional scans are possible, for example, a direct mapping between the structural scan and the functional scan could be learned from existing or simulated scans. This can be much faster than simulating the functional scan at a low level as is done with techniques such as PET-SORTEO. One simple approach is to use a direct linear mapping of intensities between the two modalities however such a technique may not be able to model the relatively complex mapping between the modalities. A more sophisticated technique is to use a texture based model such as those used in computer graphics to render objects with different texture properties. One such technique is described in *Image Analogies*, Aaron Hertzman, Charles E. Jacobs, Nuria Oliver, Brian Curless, David H Salesin *Proc. SIGGRAPH* 2001. Here a regression model is trained to map an image to another image rendered in a different style. For example, styles might include different artistic styles, lower, or higher, resolution versions of the images. For the purpose of the present invention, the virtual functional scan is considered as a different rendered style of the structural image. Thus, as shown for example in FIG. 3, a set of rules is generated (Step 302) which govern the appearance in the virtual functional scan, of given regions in a structural scan. So, for example, such a technique could be trained to render regions of white matter in the MRI brain scan with an appearance consistent with that of the same region in a PET scan (see Step 304). A low level simulator such as the PET-SORTEO algorithm referred to earlier could be used to train such techniques.

We have previously described how the reference may be generated by running the simulation process a number of times. An alternative to this approach is to modify the simulation process such that it produces an estimate of variance for each voxel in the virtual functional scan and hence only needs to be run once. There are three principal sources of variation in functional scans that need to be considered and various approaches to estimating the uncertainty associated with these. Here, for brevity, we discuss the variations associated with PET scans although similar sources of variation exist for other functional modalities.

The first type is the inherent variability or noise due to the discrete nature of the physics underlying the PET scan; specifically positron annihilations which emit coincidental photon pairs at specific energies. The result is that even if it were possible to repeat a PET scan with identical conditions, then the resulting image would be slightly different. There are known techniques in the literature for estimating this variability for specific reconstruction algorithms. For example R. E. Carson, Y. Yan et al *An approximation Formula for the Variance of PET Region-of-interest values* IEEE Trans. Med Imaging Vol 12, No 2, June 1993, pg 240-250 for FBP (linear) reconstruction methods or J. A. Fessler, "Mean and variance of implicitly defined biased estimators: applications to tomography, "*IEEE Transactions on Image Processing*, vol. 5, pp 493-506, 1996 for OSEM (non-linear). A reconstruction algorithm takes the raw measurements from the medical scanner—in the case of PET, photon counts in a particular detector—and produces an image suitable for human interpretation. Alternative methods, which are somewhat independent of reconstruction include Bootstrap (M. Dahlbom, "Estimation of Image Noise in PET Using the Bootstrap Method," *IEEE Transaction on Nuclear Science*, vol.

49, pp. 2062-2066, 2002; and M. Dahlbom, C. Schiepers, and J. Czernin, "Comparison of Noise Equivalent Count Rates and Image Noise," *IEEE transactions on nuclear science*, vol. 53, pp. 1386-1390, 2005.

The second source of variation is due to the specific scanner used and any associated imaging agent, for example FDG in PET. The third type is due to the biological state of the patient, for instance, whether they are tired or alert, their general metabolism, their heartbeat during the examination etc. Indeed, a great deal of preparation is often necessary to mitigate such effects: after injection of the imaging agent, patients are required to lie down, remain still in a dimly lit room and not talk for a period of time before imaging.

The last two sources of variation can be modeled by supplying additional information to the simulation process. One approach could be to supply Time Activity Curves and scanner parameters with variance-information.

A further processing technique is to train models that predict the output variance directly. Such training can be accomplished by examining a large set of synthesised scans generated previously (see for example S. Pajevik, M. E. Daube-Witherspoon, S Bacharach and R. E. Carson, "Noise Characteristics of 3-D and 2-D PET images, "*IEEE Trans Med Imaging*, vol. 17, pp. 9-23, 1998).

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

The invention claimed is:

1. A method of processing an actual functional medical scan of a subject and a structural medical scan of said subject to generate a data set that is representative of disease state or drug or tracer uptake of said subject, said method comprising:

synthesizing at least one functional medical scan from said structural medical scan to produce at least one virtual functional medical scan; and comparing said actual functional medical scan with said at least one virtual functional medical scan, wherein:

said synthesizing step comprises synthesizing a plurality of virtual functional medical scans representing a plurality of disease states; and said comparing step comprises comparing the actual functional medical scan with the plurality of virtual functional medical scans, to determine which of said plurality of virtual functional medical scans is most correlated, to give an indication of the disease state for the actual functional medical scan.

2. The method of claim 1, wherein:

a plurality of virtual functional scans is generated and combined to produce an average virtual functional medical scan; and the actual functional medical scan is compared with said average virtual functional medical scan.

3. The method of claim 1, wherein the actual functional medical scan and the plurality of virtual functional medical scans are compared by computing a score of normality for corresponding regions of interest.

4. The method of claim 3 wherein the score of normality is computed for corresponding voxels.

5. The method of claim 4, wherein the score of normality comprises a Z score.

6. The method of claim 1, wherein the plurality of virtual functional medical scans is generated by the steps of:

segmenting the structural medical scan into a number of tissue classes;

assigning a time-activity curve to each tissue-class; and modeling the functional behavior of each tissue class.

7. The method of claim 1, wherein a virtual functional medical scan is generated by the steps of:

generating a set of rules governing the appearance in a functional medical scan, of regions identifiable in said structural medical scan; and applying said set of rules to regions in the structural medical scan.

8. The method of claim 1, wherein the plurality of virtual functional medical scans is generated along with an estimation of variance for each voxel.

9. The method of claim 1, wherein the structural medical scan comprises a Magnetic Resonance Image.

10. The method of claim 1, wherein the structural medical scan comprises a computerized tomography scan.

11. The method of claim 1, further including the step of displaying the data set.

12. The method of claim 11, wherein the data set is displayed as a graphical image.

13. A nontransitory computer readable medium encoded with a program for a computer, said program embodying the method of claim 1.

14. A nontransitory computer readable medium comprising a data carrier storing a program according to claim 13.

15. Apparatus for processing an actual functional medical scan of a subject and a structural medical scan of said subject to generate a data set that is representative of disease state or drug or tracer uptake of said subject, said apparatus comprising:
   means for synthesizing at least one functional medical scan from the structural medical scan to produce a virtual functional scan; and
   means for comparing said actual functional medical scan with the virtual functional medical scan, wherein:
   said means for synthesizing synthesizes a plurality of virtual functional medical scans representing a plurality of disease states; and
   said means for comparing compares the actual functional medical scan with the plurality of virtual functional medical scans, to determine which of said plurality of virtual functional medical scans is most correlated, to give an indication of the disease state for the actual functional medical scan.

16. A method assessing functional medical scan data, comprising:
   acquiring a functional medical scan of a subject;
   acquiring a structural medical scan of said subject;
   synthesizing at least one functional medical scan from the structural medical scan to produce at least one virtual functional medical scan; and
comparing said acquired functional medical scan with said at least one virtual functional medical scan, wherein:
   said synthesizing step comprises synthesizing a plurality of virtual functional medical scans representing a plurality of disease states; and
   said comparing step comprises comparing the acquired functional medical scan with the plurality of virtual functional medical scans, to determine which of said plurality of virtual functional medical scans is most correlated, to give an indication of a disease state for the acquired functional medical scan.

17. The method according to claim 16, wherein at least one virtual functional medical scan represents a non-diseased state of the subject.

* * * * *